United States Patent
Zhou et al.

(10) Patent No.: US 11,864,512 B2
(45) Date of Patent: Jan. 9, 2024

(54) MEDIUM FOR TISSUE RAPID PROPAGATION OF BLUEBERRY STEM SEGMENT AND A METHOD FOR TISSUE RAPID PROPAGATION

(71) Applicant: SHANDONG DAFENGYUAN AGRICULTURE CO.,LTD., Rizhao (CN)

(72) Inventors: Yangyan Zhou, Rizhao (CN); Weijian Sun, Rizhao (CN); Wenxiu Chen, Rizhao (CN); Aowei Mo, Rizhao (CN); Peng Guo, Rizhao (CN); Penghao Xu, Rizhao (CN)

(73) Assignee: Shandong Dafengyuan Agriculture Co., Ltd., Rizhao (CN)

( * ) Notice: Subject to any disclaimer, the term of this patent is extended or adjusted under 35 U.S.C. 154(b) by 0 days.

(21) Appl. No.: 17/720,726

(22) Filed: Apr. 14, 2022

(65) Prior Publication Data
US 2022/0330507 A1 Oct. 20, 2022

(30) Foreign Application Priority Data
Apr. 16, 2021 (CN) .......................... 202110413254.6

(51) Int. Cl.
*A01H 6/36* (2018.01)
*A01H 4/00* (2006.01)
*A01G 24/15* (2018.01)
*A01G 24/22* (2018.01)
*A01G 17/00* (2006.01)

(52) U.S. Cl.
CPC ........... *A01H 4/001* (2013.01); *A01G 17/005* (2013.01); *A01G 24/15* (2018.02); *A01G 24/22* (2018.02); *A01H 4/008* (2013.01)

(58) Field of Classification Search
CPC ............................... A01H 4/001; A01G 24/15
See application file for complete search history.

(56) References Cited

FOREIGN PATENT DOCUMENTS

| CN | 102187813 A | 9/2011 |
|---|---|---|
| CN | 103125395 A | 6/2013 |
| CN | 106171980 A | 12/2016 |
| CN | 106342688 A | 1/2017 |
| CN | 108651277 A | 10/2018 |

OTHER PUBLICATIONS

Qui. 2018. Regeneration of Blueberry cultivars through indirect shoot organogensis. HortScience 53: 1045-1049. (Year: 2018).*
Schuchovski et al. 2019. In Vitro Establishment of 'Delite' Rabbiteye Blueberry Microshoots. Horticulturae). (Year: 2019).*
Chinese Notice of Authorization and Registration issued in Chinese Patent Application No. 202110413254.6 dated Jan. 29, 2022.
Chinese Office Action issued in Chinese Patent Application No. 202110413254.6 dated Dec. 10, 2021.

* cited by examiner

*Primary Examiner* — Karen M Redden
(74) *Attorney, Agent, or Firm* — United IP Counselors, LLC

(57) ABSTRACT

The invention discloses a medium combination for a rapid propagation medium for blueberry stem segment tissue, wherein the pre-culture medium takes the MS medium containing 2-(N-morpholine) ethanesulfonic acid as basic medium, comprising 0.1-0.5 mg/L IAA, 0.05-0.6 mg/L CPPU; the rapid culture medium takes the MS medium containing 2-(N-morpholine) ethanesulfonic acid as basic medium, comprising: 0.2-0.5 mg/L ZT; the seedling growth medium takes the MS medium containing 2-(N-morpholine) ethanesulfonic acid as basic medium, comprising: 0.1-2.0 mg/L 2-ip; and the rooting medium takes ½ MS medium as basis medium, comprising: 0.3-4.0 mg/L NAA. The invention further discloses a method of using the above medium combination to conduct rapid propagation of blueberry stem segment tissue, the propagation rate of this method is rapid.

9 Claims, 5 Drawing Sheets

MEDIUM FOR TISSUE RAPID PROPAGATION OF BLUEBERRY STEM SEGMENT AND A METHOD FOR TISSUE RAPID PROPAGATION

BACKGROUND

Field of Invention

The present invention belongs to the field of plant tissue culture, relates to a medium for tissue rapid propagation of blueberry stem segment and a method for tissue rapid propagation.

Background of the Invention

Blueberry (*Vaccinium* SPP) is a perennial low shrubof vaccinium, ericaceae, which is native to North America and East Asia, distributed in North Korea, Mongolia, Europe, North America and areas of Heilongjiang, Inner Mongolia, Jilin, Changbaishan and the like in China. The blueberry fruit is rich in nutrients and anthocyanin, and has function of preventing brain nerve aging, strong heart, anti-cancer, softening blood vessels, and enhancing human immunity and the like. Because of its superior healthcare value, it is popular in the world and one of the five healthy fruits recommended by the World Food and Agriculture Organization.

The Chinese patent application under application No. 201710196339.7 discloses a primary and subculture medium for blueberry tissue culture, but the method cannot fully meet the demand for blueberry tissue culture.

SUMMARY

In order to solve the problems exist in the prior art, the first aspect of the invention provides a medium combination for a rapid propagation for blueberry stem segment tissue, the medium combination comprises pre-culture medium, rapid culture medium, seedling growth medium and rooting medium;

The pre-culture medium takes the MS medium containing 2-(N-morpholine) ethanesulfonic acid as basic medium, the pre-culture medium comprises: 0.1-0.5 mg/L (for example, 0.12 mg/L, 0.14 mg/L, 0.16 mg/L, 0.18 mg/L, 0.20 mg/L, 0.22 mg/L, 0.24 mg/L, 0.26 mg/L, 0.28 mg/L, 0.30 mg/L, 0.32 mg/L, 0.34 mg/L, 0.36 mg/L, 0.38 mg/L, 0.40 mg/L, 0.42 mg/L, 0.44 mg/L, 0.46 mg/L, 0.48 mg/L) IAA and 0.05-0.6 mg/L (for example, 0.06 mg/L, 0.08 mg/L, 0.10 mg/L, 0.12 mg/L, 0.14 mg/L, 0.16 mg/L, 0.18 mg/L, 0.20 mg/L, 0.22 mg/L, 0.24 mg/L, 0.26 mg/L, 0.28 mg/L, 0.30 mg/L, 0.32 mg/L, 0.34 mg/L, 0.36 mg/L, 0.38 mg/L, 0.40 mg/L, 0.42 mg/L, 0.44 mg/L0.46 mg/L, 0.48 mg/L, 0.50 mg/L, 0.52 mg/L, 0.54 mg/L, 0.56 mg/L, 0.58 mg/L) CPPU;

the rapid culture medium takes the MS medium containing 2-(N-morpholine) ethanesulfonic acid as basic medium, the rapid culture medium comprises: 0.2-0.5 mg/L (for example, 0.22 mg/L, 0.24 mg/L, 0.26 mg/L, 0.28 mg/L, 0.30 mg/L, 0.32 mg/L, 0.34 mg/L, 0.36 mg/L, 0.38 mg/L, 0.40 mg/L, 0.42 mg/L, 0.44 mg/L, 0.46 mg/L, 0.48 mg/L) ZT;

the seedling growth medium takes the MS medium containing 2-(N-morpholine) ethanesulfonic acid as basic medium, the seedling growth medium comprises: 0.1-2.0 mg/L (for example, 0.2 mg/L, 0.3 mg/L, 0.4 mg/L, 0.5 mg/L 0.6 mg/L, 0.7 mg/L, 0.8 mg/L, 0.9 mg/L, 1.0 mg/L, 1.1 mg/L, 1.2 mg/L, 1.3 Mg/L, 1.4 mg/L, 1.5 mg/L, 1.6 mg/L, 1.7 mg/L, 1.8 mg/L, 1.9 mg/L) 2-ip; and the rooting medium takes ½ MS medium as basis medium, the rooting medium comprises: 0.3-4.0 mg/L (for example, 0.4 mg/L, 0.6 mg/L, 0.8 mg/L, 1.0 mg/L, 1.2 mg/L, 1.4 mg/L, 1.6 mg/L, 1.8 mg/L, 2.0 mg/L, 2.2 mg/L, 2.4 mg/L, 2.6 mg/L, 2.8 mg/L, 3.0 mg/L, 3.2 mg/L, 3.4 mg/L, 3.6 mg/L, 3.8 mg/L) NAA.

In some embodiments, the pre-culture medium further comprises: 25-150 mg/L NaCl.

In some embodiments, the pre-culture medium comprises: 50-100 mg/L NaCl.

In some embodiments, the pre-culture medium comprises: 0.15-0.3 mg/L IAA and 0.05-0.3 mg/L CPPU.

In some embodiments, the pre-culture medium comprises: 0.2 mg/L IAA and 0.1 mg/L CPPU.

In some embodiments, in the pre-culture medium, the concentration of 2-(N-morpholine) ethanesulfonic acid is 20 mg/L.

In some embodiments, in the pre-culture medium, the MS medium comprises 4-8 g/L agar and 15-30 g/L sucrose.

In some embodiments, in the pre-culture medium, pH=5.0-5.5. In some embodiments, the rapid culture medium further comprises: 0.5-1.5 mg/L putrescine and/or 0.5-1.5 mg/L spermine.

In some embodiments, the rapid culture medium further comprises: 0.5-1.5 mg/L spermidine.

In some embodiments, the rapid culture medium comprises: 0.3-0.5 mg/L ZT.

In some embodiments, the rapid culture medium comprises: 0.4 mg/L ZT.

In some embodiments, in the rapid culture medium, the concentration of 2-(N-morpholine) ethanesulfonic acid is 20 mg/L.

In some embodiments, in the rapid culture medium, the MS medium comprises 4-8 g/L agar and 25-35 g/L sucrose.

In some embodiments, in the rapid culture medium, pH=5.0-5.5.

In some embodiments, the seedling growth medium comprises: 0.3-0.7 mg/L 2-ip.

In some embodiments, the seedling growth medium comprises: 0.5 mg/L 2-ip.

In some embodiments, in the seedling growth medium, the concentration of 2-(N-morpholine) ethanesulfonic acid is 20 mg/L.

In some embodiments, in the seedling growth medium, the MS medium comprises 4-8 g/L agar and 25-35 g/L sucrose.

In some embodiments, the seedling growth medium, pH=5.0-5.5.

In some embodiments, the rooting medium comprises: 1.0-3.0 mg/L NAA.

In some embodiments, the rooting medium comprises: 2.0 mg/L NAA.

In some embodiments, in the rooting medium, the ½ MS medium comprises 4-8 g/L agar and 25-35 g/L sucrose.

In some embodiments, in the rooting medium, pH=5.0-5.5.

The second aspect of the present invention provides a method of rapid propagation of blueberry stem segment tissue, the method comprises the following steps:

S1: inoculating the sterile blueberry stem segment with a bud point into the pre-culture medium in the medium combination of the first aspect of the present invention to conduct pre-culture to obtain a pre-cultured blueberry stem segment;

S2: inoculating the pre-cultured blueberry stem segment into the rapid culture medium in the medium combination of the first aspect of the present invention to conduct rapid culture to obtain a rapid cultured blueberry seedlings;

S3: inoculating the rapid cultured blueberry seedlings into the seedling growth medium in the medium combination of the first aspect of the present invention to conduct continue culture to obtain a further cultured blueberry seedlings;

S4: inoculating the further cultured blueberry seedlings into the rooting medium in the medium combination of the first aspect of the present invention to conduct continue culture to obtain a blueberry tissue culture seedlings.

In some embodiments, in step S1, the sterile blueberry stem segment is from the blueberry tissue culture seedlings.

In some embodiments, in step S1, the condition of pre-culture is to culture in dark environment at 10-20° C. for 1-4 hours, and then culture under light conditions for 1-3 days.

In some embodiments, in step S1, the light time falls in a range of 14-18 hours a day.

In some embodiments, in step S1, the light intensity falls in a range of 1500-3000 lx.

In some embodiments, in step S1, in the culture under light conditions, the culture environment humidity falls in a range of 50-70%.

In some embodiments, in step S2, the culture temperature falls in a range of 20-28° C.

In some embodiments, in step S2, the culture light time falls in a range of 14-18 hours a day.

In some embodiments, in step S2, the culture light intensity falls in a range of 1500-3000 lx.

In some embodiments, in step S2, the culture environment humidity falls in a range of 50-70%.

In some embodiments, in step S2, the culture time falls in a range of 15-20 days.

In some embodiments, in step S3, the culture temperature falls in a range of 20-28° C.

In some embodiments, in step S3, the culture light time falls in a range of 14-18 hours a day.

In some embodiments, in step S3, the culture light intensity falls in a range of 1500-3000 lx.

In some embodiments, in step S3, the culture environment humidity falls in a range of 50-70%.

In some embodiments, in step S3, the culture time falls in a range of 10-20 days.

In some embodiments, in step S4, the culture temperature falls in a range of 20-28° C.

In some embodiments, in step S4, the culture light time falls in a range of 14-18 hours a day.

In some embodiments, in step S4, the culture light intensity falls in a range of 1500-3000 lx.

In some embodiments, in step S4, the culture environment humidity falls in a range of 50-70%.

In some embodiments, in step S4, the culture time falls in a range of 20-30 days.

In some embodiments, the method further comprises: conducting seedling hardening and transplanting to the blueberry tissue culture seedlings, to obtain blueberry cultivated plant.

In some embodiments, the step of the seedling hardening comprises: maintaining the humidity of the inside of the culture bottle of the blueberry tissue culture seedlings to be 65-75% for 0.5-1.5 days, then maintaining the humidity to be 55-65% for 5-9 days under ventilation condition.

In some embodiments, in the step of the seedling hardening, the light time falls in a range of 14-18 hours a day.

In some embodiments, in the step of the seedling hardening, the light intensity falls in a range of 1500-3000 lx.

In some embodiments, cleaning and removing the medium from the root of the blueberry plant after seedling hardening, to conduct the transplanting.

In some embodiments, the culture soil for transplanting is vermiculite, nutritious soil and moss in mass ratio of 1:0.5-1.5:0.5-1.

The techniques of the present invention are beneficial to prior art:

At present, most of the production of blueberry tissue culture seedlings adopt the subculture propagation mode of cutting the blueberry seedling to conduct propagation. With the subculture time increases, the state and quality of seedlings will decreased gradually, it requires replacing maternal seedling, and the time for culturing a batch of seedling is longer, which is 7-8 weeks. The present invention takes the stem segment of blueberry tissue culture seedlings as material to conduct tissue culture seedling production, 150 stem segments can be placed in the medium of one bottle, each stem segment can be grown to at least one plant of blueberry seedling, which shortens the propagation time and enhance the reproduction efficiency; at the time of pre-culture, by conferring slight reverse stress to the stem segment, the grown tissue culture seedling is stronger, the cultured blueberry seedling is fast in growth and good in quality; it increases the growth rate of tissue culture seedling by rapid medium; moreover, only the time about 5 weeks will conduct rooting and seedling hardening to the cultured tissue culture seedlings, which greatly shortens the time of culture of tissue culture seedlings.

In Examples 2 and 3 of the present invention, there is neither callus induction step, nor the step of budding via callus. The blueberry seedlings are directly germinated from the blueberry stem segment, because each blueberry has a bud point, which can be germinated to be blueberry seedling. The present invention takes the stem segment of blueberry as material to conduct propagation, but not the conventional entire tissue culture seedling material widely adopted at present, this is the propagation mode modified according to the growth character of the blueberry tissue culture seedlings in the present invention. As compared with the conventional blueberry rapid propagation mode in Example 1, such method shortens propagation time apparently, and each seedling is grown from a but point, which ensures the quality of the seedling.

DETAILED DESCRIPTION OF THE EMBODIMENTS

Figure 1:
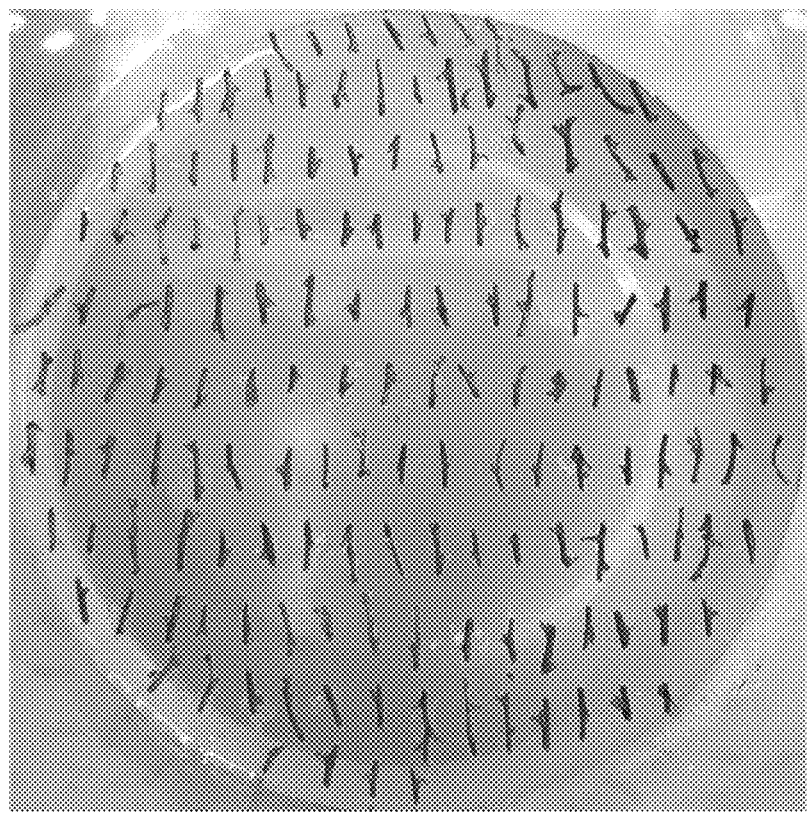
FIG. 1 shows the stem segment after dark pretreatment.

In order to make the purpose, technical solutions and advantages of the present invention more clear, the embodiments of the present invention will be further described in details in combination with Figures bellow.

In the present invention, all the steps not described in details are conventional operations in the art, and all materials not recorded in details are conventional materials in the art.

Definition: the time for culturing a batch of seedlings refers to the time from the initiating culture to the time prior to rooting, i.e., the time interval from the pre-culture to be grown to be the tissue culture seedling that can be rooted, or a time interval between two subculture.

Example 1: Blueberry Routine Tissue Culture (One) Selection of Explant

Selecting the blueberry (variety: JE) of the field as the mother plant, selecting the robust annual branch to be germinated, and using scissors to cut it down.

(Two) Pre-Treatment of Explant

Cutting off the apical bud of the explant, using sealing film to seal the top wound, putting the branch into clean water for culturing 7 days (room temperature falls in a range of 22-24° C., the light intensity falls in a range of 1500-3000 lx, relative humidity falls in a range of 60-70%, 16/8 h light cycle), to the state that the bud will be germinated. Using a fine hair brush to dip detergent to clean the dust on branch and the surface of bud, and put the branches under the flow of water to be rinsed for 30 minutes, using scissors to cut the branches into the small stem segment with bud, and then placing it into the sterile ultra-clean workbench, the subsequent operations needs the sterile operation to be operated in sterile ultra-clean workbench.

(Three) Disinfection of the Explant

Preparing 100 mL alcohol of 75 v/v % in concentration and 2 w/v % sodium hypochlorite, adding 1-2 drops Tween-20 into each, shaking uniformly for use, respectively.

Using the 75 v/v % alcohol containing Tween-20 to disinfect the small stem segment with bud for 20 s, using sterilized deionized water to rinse 3 times, then using the 2 w/v % sodium hypochlorite containing Tween-20 to make disinfection for 8 s, after disinfection, using sterilized deionized water to rinse 5 times, until there has no apparent flavor of sodium hypochlorite. Using sterilized filter paper to suck the extra moisture on the bud, for use.

(Four) Culture of the Explant

Using anatomical tweezers to peel off the scales exterior of bud slightly on the sterilized filter board, inoculating the explant into the primary medium containing 0.5 mg/L IBA (WPM medium, containing 30 g/L sucrose, 7 g/L agar, pH is 5.2), to let the explant germinate. (The culture conditions fall in a range of 22-25° C., light intensity falls in a range of 1500-3000 lx, relative humidity falls in a range of 60-70%, 16/8 h light cycle).

(Five) Subculture and Multiplication of Tissue Culture Seedlings

When the bud is grown to 1.5-2 cm, cutting the bud off in ultra-clean workbench, put it in the proliferation medium (WPM medium, containing 30 g/L sucrose, 7 g/L agar, pH is 5.2) containing 0.5 mg/L IBA, 0.2 mg/L 6-BA, 0.2-0.4 mg/L ZT (the amount of ZT can be properly adjusted according to the growth of the seedling of different varieties) to continue subculture and propagate, according to the growth condition of the tissue culture seedlings, subculture once every 6-8 weeks. (The culture conditions fall in a range of 22-25° C., light intensity falls in a range of 1500-3000 lx, relative humidity falls in a range of 60-70%, 16/8 h light cycle).

(Six) Rooting Culture

Choosing the robust tissue culture seedlings of step (five) grown for 6-7 weeks, cutting off callus lumps of the bottom, put it into the medium containing 0.8 mg/L NAA (½ MS medium, containing 20 g/L sucrose, 6 g/L agar, pH falls in a range of 5.2-5.4) to perform rooting culture (culture conditions fall in a range of 22-25° C., light intensity falls in a range of 1500-3000 lx, relative humidity falls in a range of 60-70%, 16/8 h light cycle). Seedling hardening can be performed after 4-5 weeks.

(Seven) Seedling Hardening Culture

Opening the bottle cap of tissue culture bottle of the rooted tissue culture seedling to the semi-open state, placing it into seedling hardening room for culture 1 d (relative humidity is 80%, lighting strength is 1500 lx, 22-24° C.), then open the cap of tissue culture bottle, culturing it in seedling hardening room for culturing 6 d. During the period, gradually reducing the air humidity (gradually decreasing from the initial 80% to 50%, decreasing once each 2-3 d) and gradually increasing light intensity (gradually increasing from the initial 1500 lx to 3000 lx, enhancing once every two days) according to the growth state of seedling. Increasing the temperature gradually from 22° C. to 25° C. 16/8 h light cycle.

(Eight) Transplanting

Taking out the blueberry plants after seedling hardening from the bottle, removing the medium, using water to wash the root, sowing the plant into nutrition pot. The culture soil for transplanting is vermiculite: nutritious soil: moss (1:1:1 in mass ratio), pay attention to control the pH of nutrient soil to fall in a range of 5.3-5.6.

Example 2: Blueberry Tissue Culture (One) Formulation of MS Medium Containing MES See Table 1 for the formulation of MS basic medium containing 2-(N-morpholine) ethanesulfonic acid (MES) of the present invention.

TABLE 1 the formulation of MS basic medium containing 2-(N-morpholine) ethanesulfonic acid (MES)

| Classification | Ingredient | Content mg/L |
|---|---|---|
| Macroelement | Ammonium Nitrate, $NH_4NO_3$ | 825 |
| | Magnesium Sulfate Heptahydrate, $MgSO_4 \cdot 7H_2O$ | 370 |
| | Potassium Nitrate, $KNO_3$ | 950 |
| | Potassium Dihydrogen Phosphate, $KH_2PO_4$ | 170 |
| | Calcium chloride dihydrate, $CaCl_2 \cdot 2H_2O$ | 220 |
| Microelement | Boric acid, $H_3BO_3$ | 6.2 |
| | Zinc Sulfate Heptahydrate, $ZnSO_4 \cdot 7H_2O$ | 8.6 |
| | Manganese Sulfate Monohydrate, $MnSO_4 \cdot H_2O$ | 22.3 |
| | Sodium Molybdate Dihydrate, $NaMo_4 \cdot 2H_2O$ | 0.25 |

TABLE 1-continued the formulation of MS basic medium containing 2-(N-morpholine) ethanesulfonic acid (MES)

| Classification | Ingredient | Content mg/L |
|---|---|---|
| | Copper Sulfate Pentahydrate, $CuSO_4 \cdot 5H_2O$ | 0.025 |
| | Potassium iodide, KI | 0.83 |
| | Cobalt chloride hexahydrate, $CoCl_2 \cdot 6H_2O$ | 0.025 |
| Ferric Salt | Ethylenediamine dihydroxyphenyl sodium iron acetate | 40 |
| Other Organics | MES | 20 |
| | Inositol | 100 |
| | Glycine | 2 |
| | Thiamine Hydrochloride | 0.1 |
| | Niacin | 0.5 |
| | Pyridoxine Hydrochloride | 0.5 |

(Two) Preparation of Pre-Culture Medium and Blueberry Pre-Culture (1) Preparation of Pre-Culture Medium:

All the #1-#9 pre-culture medium of the present invention take the MS basic medium containing MES shown in table 1 as basic medium, pH is 5.2, other ingredients in formulation are shown in columns 2-4 of Table 2.

(2) Blueberry Pre-Culture

Figure 2:
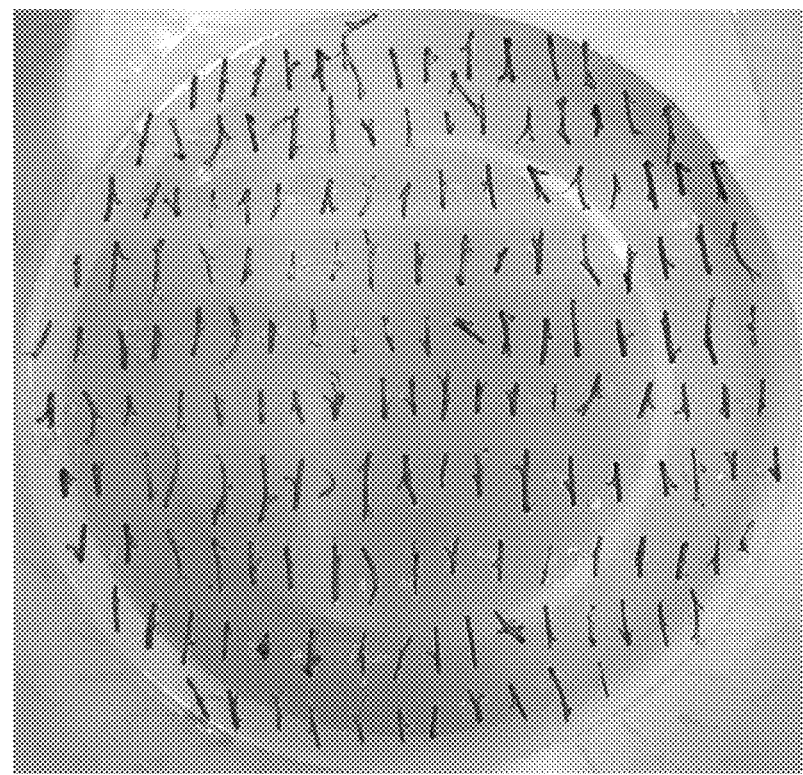
FIG. 2 shows the pre-treated blueberry stem segment.

The specific method of operation is as follows: putting the stem segment of the blueberry sterile tissue culture seedling obtained by step (six) of Example 1 on the #1-#4 pre-culture medium for pre-culture. There are at least one bud point on each blueberry stem segment. The interval among the stem segments is not less than 0.5 mm, and putting the stem segment at 16° C. for dark treatment for 2 h (all 2-4 h are acceptable), see FIG. 1 for the photo of one bottle therein. It was then placed in the environment of 16 hours lighting/8 hours dark per day and a relative humidity of 60% for culturing 2 d (1-2 d). See FIG. 2 for the photo of one bottle (no germination), counting the germination rate of stem segment and the state after germination during the rapid culture process, see Table 2 for culture effect.

Groping the #1-#4 pre-culture medium by the above experiments, and selecting that the best hormone combination is the hormone combination of #1 pre-culture medium.

Using the same method to perform pre-culture, the difference lies in that changing the above #1 pre-culture medium to #5 pre-culture medium, see Table 2 for culture effect. The germination rate is only reduced by 1%, and the growth state has little difference, in order to reduce cost, selecting sucrose concentration of 10 g/L for further test.

Adding three concentrations of NaCl on the basis of #5 pre-culture medium to obtain #6-#8 pre-culture medium to conduct salt stress, and the pre-culture conditions were the same as those of the #1-#4 pre-culture medium, see Table 2 for culture effect. As can be seen, as compared with the pre-culture with #5 pre-culture medium, 200 mg/L NaCl stress will significantly deteriorate the culture effect, while the stress growth states between 50 mg/L NaCl and 100 mg/L NaCl are different slightly, and germination rate will be significantly higher, and the culture effect of 100 mg/L NaCl stress is best.

TABLE 2

Pre-culture medium and culture effect

| Numbering | The combination of different hormones | Sucrose g/L | Agar g/L | Other ingredients and the contents | The germination rate of stem segment in the process of rapid culture | The state after germination |
|---|---|---|---|---|---|---|
| 1 | 0.2 mg/L IAA, 0.1 mg/L CPPU | 20 | 7 | null | 68% | +++ |
| 2 | 0.2 mg/L IAA, 0.5 mg/L CPPU | 20 | 7 | null | 64% | ++ |
| 3 | 0.4 mg/L IAA, 0.1 mg/L CPPU | 20 | 7 | null | 57% | ++ |
| 4 | 0.4 mg/L IAA, 0.5 mg/L CPPU | 20 | 7 | null | 49% | + |
| 5 | 0.2 mg/L IAA, 0.1 mg/L CPPU | 10 | 7 | null | 67% | +++ |
| 6 | 0.2 mg/L IAA, 0.1 mg/L CPPU | 10 | 7 | 50 mg/L NaCl | 85% | +++ − |
| 7 | 0.2 mg/L IAA, 0.1 mg/L CPPU | 10 | 7 | 100 mg/L NaCl | 93% | +++ − |
| 8 | 0.2 mg/L IAA, 0.1 mg/L CPPU | 10 | 7 | 200 mg/L NaCl | 43% | + −− |

Note:
"+" indicates the growth state of buds.
+ indicates that the status is not good, grows slow
++ indicates that status is common
+++ indicates that the status is good, the growth is rapid
"−" indicates the state that buds are stressed.
− indicates slight stressed phenotype
−− indicates severe stressed phenotype In this step, using blueberry aseptic tissue culture seedling is for saving the step of explant disinfection treatment, to improve efficiency, increase the aseptic effect, and promote the continuity of production. The present invention can also use robust and young blueberry stem segment, and obtain aseptic blueberry stem segment by conventional disinfection for the subsequent aseptic operations.

The stem segment obtained by step (three) of Example 1 can also be adopted to perform subsequent operations.

(Three) Preparation of Rapid Culture Medium and Rapid Culture (1) Preparation of Rapid Culture Medium All the #1-#6 rapid culture medium of the present invention take the MS basic medium containing MES as basic medium, which comprises 30 g/L sucrose and 7 g/L agar, pH is 5.2, other ingredients in formulation are shown in Table 3.

(2) Rapid Culture

Figure 3:
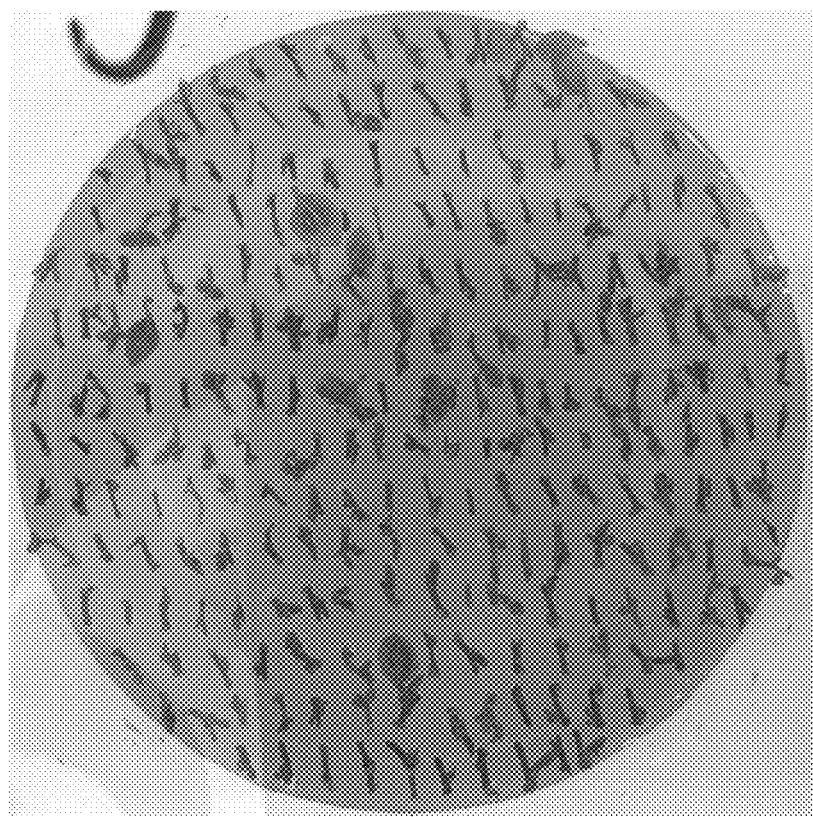
FIG. 3 shows the blueberry stem segment upon rapid culture for 5 days.
Figure 4:
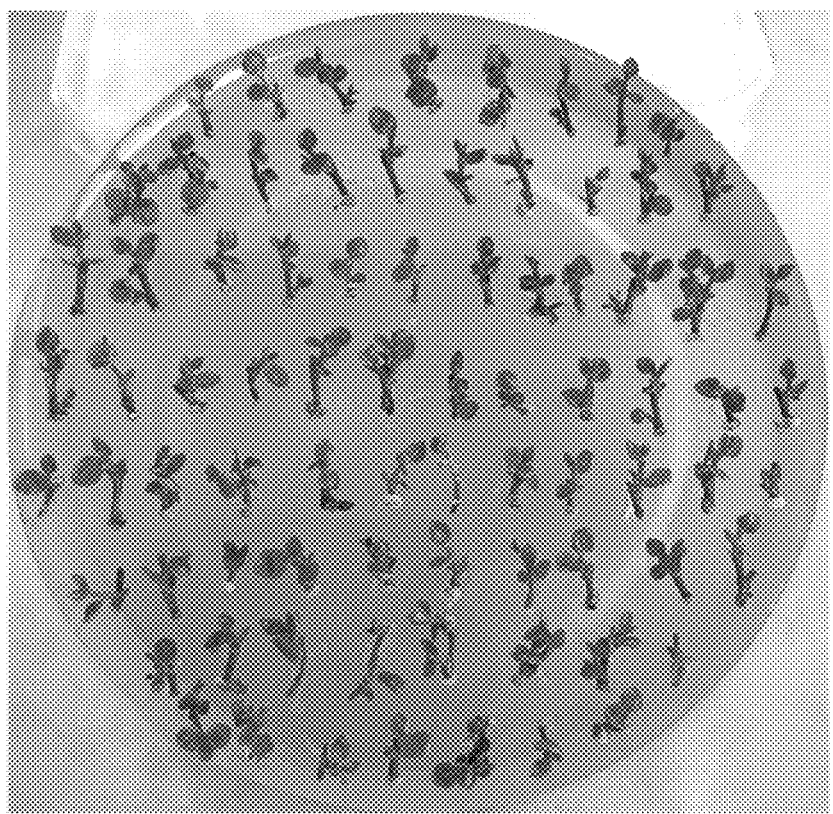
FIG. 4 shows the blueberry stem segment upon rapid culture for 13 days, and the axillary bud has been obviously germinated.

The specific method of operation is as follows: after the pre-culture is completed, transferring the stem segment pre-cultured with #7 pre-culture medium to #1-#2 rapid culture medium, and the interval among the stem segments is not less than 0.5 mm, and placing them in the environment of 24° C., 16 hours light/8 hours dark per day, the light intensity falls in a range of 1500-3000 lx, and the relative humidity is 60% to conduct culture for 15-20 d. Wherein, see FIG. 3 for the photo of a bottle of rapid culture for 5 d, see FIG. 4 for the photo of a bottle of rapid culture for 13 d, see FIG. 5 for the photo of a bottle of rapid culture for 15 d, see FIG. 6 for the photo of a bottle of rapid culture for 20 d, see Table 3 for culture effect.

As can be seen, the effect cultured by the #2 rapid culture medium is better.

Using the same method to conduct rapid culture, the difference lies in that different additives are added into the #2 rapid culture medium to form #3-#6 rapid culture medium, see Table 3 for culture effect.

As can be seen, as compared with the effect cultured by the #2 rapid culture medium, the effect of #4 rapid culture medium is deteriorated, and the culture effect of #3 and #5 rapid culture mediums are equivalent, and the effect cultured by #6 rapid culture medium is better.

TABLE 3

Rapid medium and culture effect

| Numbering | The combination of different hormones | Other ingredients and the contents | Culture effect |
| --- | --- | --- | --- |
| 1 | 0.2 mg/L ZT | null | + |
| 2 | 0.4 mg/L ZT | null | ++ |
| 3 | 0.4 mg/L ZT | 1 mg/L Putrescine | ++ |
| 4 | 0.4 mg/L ZT | 1 mg/L Spermidine | + |
| 5 | 0.4 mg/L ZT | 1 mg/L Spermine | ++ |
| 6 | 0.4 mg/L ZT | 1 mg/L Putrescine, 1 mg/L Spermidine, 1 mg/L Spermine | +++ |

Note:
+ indicates the growth rate of seedlings
+ indicates that the growth is common, growth slower,
++ indicates that the growth is good, the growth is rapid
+++ indicates that the growth is comparatively good, the growth is rapid (4) Preparation of Seedling Growth Medium and Seedling Growth (1) Seedling Growth Medium All the #1-#5 stem segment growth medium of this step take the MS medium containing MES as basic medium, which comprises 30 g/L sucrose and 7 g/L agar, pH is 5.2, other ingredients in formulation are shown in Table 4.

(2) Seedling Growth

The specific method of operation is as follows: after the rapid culture is completed, transferring the densely placed stem segment of blueberry seedling cultured by #6 rapid culture medium into #1-#5 seedling growth medium, they are cultured under the environment of 24° C., 16 hours light/8 hours dark per day, the light intensity falls in a range of 1500-3000 lx, and the relative humidity is 60%, the rooting culture can be conducted about 15 d.

Figure 7:
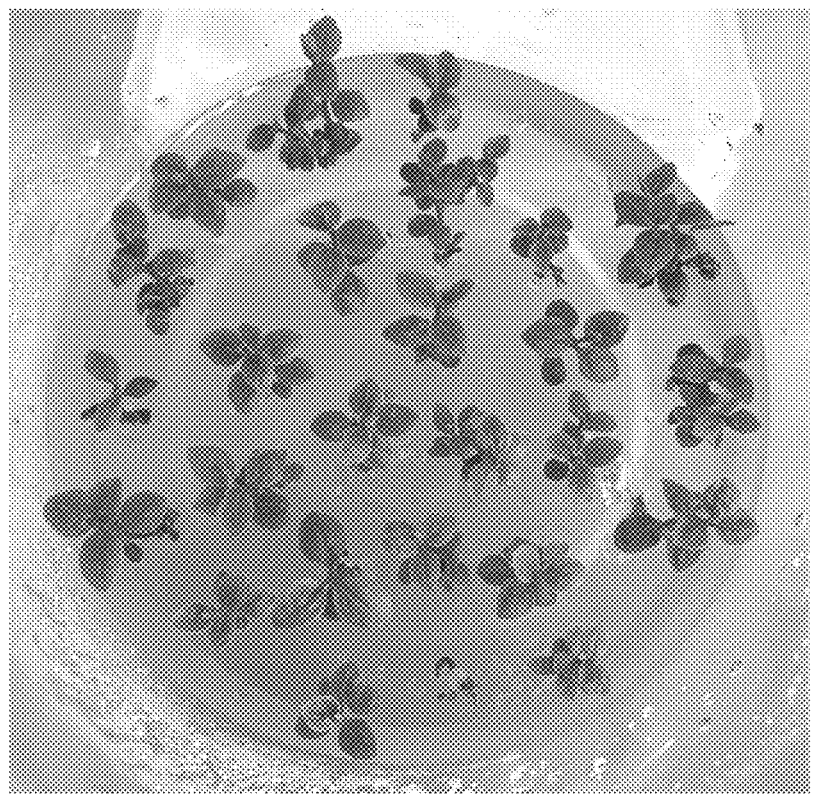
FIG. 7 shows the blueberry stem segment transplanted to a growth medium to culture.
Figure 8:
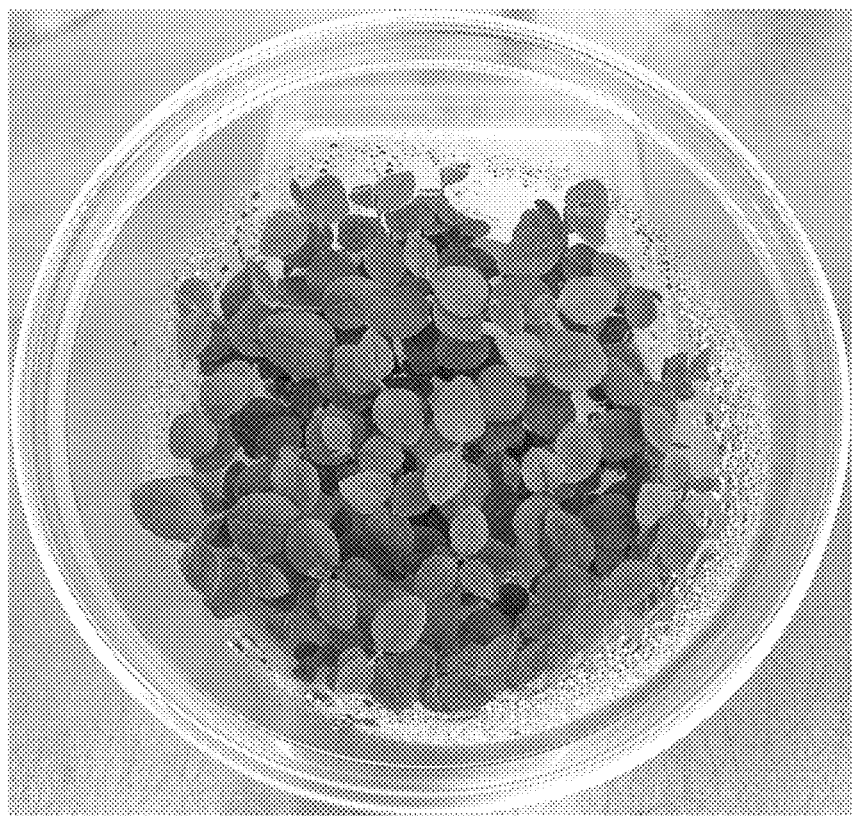
FIG. 8 shows the blueberry stem segment grown for 10 days on a growth medium.
Figure 9:
FIG. 9 shows a blueberry stem segment grown for 20 days on a growth mediums.

See FIGS. 7 and 8-9 for the culture photos of three bottles, see Table 4 for culture effect.

As can be seen, the effect cultured by the #2 seedling growth medium is the best.

Note: when placing the above stem segment, the number and interval of the stem segment placed on each medium can be properly adjusted according to the size and length of the stem segment.

TABLE 4

Seedling growth medium and culture effect

| Numbering | The combination of different hormones | The condition of tissue culture seedling growth |
| --- | --- | --- |
| 1 | 0.1 mg/L Isopentene Adenine | + |
| 2 | 0.5 mg/L Isopentene Adenine | +++ |
| 3 | 1.0 mg/L Isopentene Adenine | ++ |
| 4 | 1.5 mg/L Isopentene Adenine | ++ |
| 5 | 2.0 mg/L Isopentene Adenine | + |

Note:
"+" indicates the growth state of seedlings.
+ indicates that the growth is common, growth slower, the plant is moderate, leaf is smaller
++ indicates that the growth is good, the plant is robust
+++ indicates that the growth is comparatively good, comparatively robust, the leaves are large and glossy, and the leaves are light green.

If the explant stem segment except the tissue culture seedling used in the stage of the pre-culture in step (two), the following step is necessary:

When the axillary bud germinates and grows to 1-1.5 cm, cutting it down and placing it to the new seedling growth medium to conduct culture.

(Five) Preparation of Rooting Medium

All of the #1-#4 rooting medium of this step take ½ MS medium as basic medium, which contains 2.0 mg/L NAA, 20 g/L sucrose, 6.0 g/L agar, pH falls in a range of 5.2-5.4, other ingredients in formulation are shown in Table 5.

The specific operation method is as follows: after cutting the strongly grown blueberry seedlings cultured in #2 seedling growth medium in step (four), moving them respectively to the 4 kinds of blueberry rooting medium shown in table 5, 8-10 plants each bottle. The culture environment is 24° C., the light intensity falls in a range of 1500-3000 lx, and 16 hours lighting/8 hours dark per day. Culturing for 20-30 days, observing the rooting state of seedling and recording the rooting rate. See Table 5 for rooting rate.

As can be seen, the effect cultured by the #3 rooting medium is best.

½MS medium specifically further comprises macroelement such as 950 mg/L Potassium Nitrate, 166.1 mg/L Calcium Chloride, 825 mg/L Ammonium Nitrate, 90.35 mg/L Magnesium Sulfate, 85 mg/L Potassium Dihydrogen Phosphate; microelement such as 0.025 mg/L Copper Sulphate, 6.2 mg/L Boric Acid, 16.9 mg/L Manganese Sulfate, 0.25 mg/L Sodium Molybdate, 8.6 mg/L Zinc Sulfate, 0.025 mg/L Cobalt Chloride, 0.83 mg/L Potassium Iodide; ferric salts such as 27.8 mg/L $FeSO_4 \cdot 7H_2O$, 37.26 mg/L $Na_2$-$EDTA \cdot 2H_2O$; organics such as 2.0 mg/L Glycine, 100 mg/L Inositol, 0.50 mg/L Niacin, 0.1 mg/L Thiamine Hydrochloride (VB1), 0.5 mg/L Pyridoxine Hydrochloride (VB6).

TABLE 5

Rooting medium

| Numbering | NAA (mg/L) | Rooting rate(%) | Growth sate |
| --- | --- | --- | --- |
| 1 | 0.5 | 68% | Rooting is slow |
| 2 | 1.0 | 71% | Adventitious root is more |
| 3 | 2.0 | 93% | Rooting time is short, adventitious root is more |
| 4 | 3.0 | 83% | Rooting time is short, adventitious root is more |

(Six) Seedling Hardening

Conducting seedling hardening culture to the rooted blueberry plant of step (five), the step of seedling hardening comprises: preparing the blueberry tissue culture seedlings that have been rooted, open the cap of tissue culture bottle, adding 15 mL aseptic water therein, placing it in an environment where humidity is 70%, 1 day later, pouring off the water in the tissue culture bottle, and re-adding 20 mL of sterile water, adjusting the humidity to 60% and performing the ventilation, transplanting 7 days later, the sterile water can be replaced once during the period. The above light dark cycle is 16 hours light/8 hours darkness.

(Seven) Transplanting

Taking out the blueberry plants after seedling hardening from the bottle, removing the medium, using water to wash the root, sowing the plant into nutrition pot. The culture soil for transplanting is vermiculite: nutritious soil: moss (1:1:1 in mass ratio), pay attention to control the pH of nutrient soil to fall in a range of 5.3-5.6.

Example 3: Blueberry Tissue Culture (Through the Culture of Explant)

(One) Selection and Treatment of Explant

Selecting the twig born in the year of blueberry (variety: JE) of the field, removing leaves, using soft bristle toothbrush to dig detergent to clean the impurities of dust and the like on branch surface and put the branches under the flow of water to be rinsed for 30-40 minutes.

(Two) Disinfection of Explant

1. Preparing 100 mL alcohol of 75 v/v % (70 v/v %-75 v/v %) in concentration, adding 1-2 drops Tween-20, shaking uniformly for use; preparing 100 mL sodium hypochlorite of 2 w/v % (1.5 w/v-%-2.5 w/v %) in concentration, adding 1-2 drops Tween-20, shaking uniformly for use.

2. Cut the branches into a stem segment of moderate length to ensure that each branch section includes an axillary bud, and the distance between axillary bud and the lower end of stem segment is at least 0.5 cm.

3. Put the well-cut stem segment into the previously prepared 75 v/v % alcohol for disinfecting for 20 s (20-40 s, no more than 1 min), and slowly shaking to achieve a better disinfection effect.

4. Pour alcohol off and add sterilized deionized water to clean twice (2-3 times).

5. Adding the prepared sodium hypochlorite solution for disinfecting for 5 min (5-8 min), slowly shaking to achieve a better disinfection effect.

6. Pour the sodium hypochlorite solution, using sterilized deionized water to wash 4-5 times, until there has no flavor of sodium hypochlorite. Put the stem segment on the sterilized filter panel to absorb excess moisture, for use.

(Three) Pre-Culture of Explant

Placing the stem segment on a stem segment pre-culture medium to conduct pre-culture, wherein the pre-culture medium takes MS medium containing MES as basic medium (see Table 1 for ingredients), comprising 0.2 mg/L IAA, 0.1 mg/L CPPU, 10 g/L sucrose, 100 mg/L NaCl, 7 g/L agar, pH is 5.2. The interval among the stem segments is not less than 0.5 mm, and putting the stem segment at 16° C. for dark treatment for 2 h (2-4 h). It was then placed in the environment of 16 hours lighting/8 hours dark per day, the light intensity falls in a range of 1500-3000 lx, and a relative humidity of 60% for culturing for 2 d (1-2 d).

(Four) Stem Segment Rapid Culture

After the pre-culture, transferring the stem segment to rapid medium, wherein the rapid culture medium takes MS medium containing MES as basic medium, comprising 0.4 mg/L ZT, 1 mg/L putrescine, 1 mg/L spermidine, 1 mg/L spermine, 30 g/L sucrose, 7 g/L agar, pH is 5.2. The interval among the stem segments is not less than 0.5 mm, and placed them in the environment of 24° C., 16 hours light/8 hours dark, the light intensity falls in a range of 1500-3000 lx, and the relative humidity is 60% to conduct culture for 15-20 d.

(Five) Stem Segment Growth Culture

After the rapid culture is completed, transferring the densely placed stem segment into seedling growth medium, wherein seedling growth medium takes MS medium containing MES as basic medium, comprising 0.5 mg/L isopentene adenine, 30 g/L sucrose, 7 g/L agar, pH is 5.2. And placed them in the environment of 24° C., they are cultured under the environment of 16 hours light/8 hours dark per day, the light intensity falls in a range of 1500-3000 lx, and the relative humidity is 60%, the rooting culture can be conducted about 15 d.

Note: when placing the above stem segment, the number and interval of the stem segment placed on each medium can be properly adjusted according to the size and length of the stem segment.

(Six) Rooting Culture

After cutting the strongly grown blueberry seedlings in step (five), moving them respectively to rooting medium for rooting culture, wherein the rooting medium takes ½ MS medium as basic medium, comprising 2.0 mg/L NAA, 20 g/L sucrose, 6.0 g/L agar, pH is 5.2-5.4. 8-10 plants each bottle, the culture environment is 24° C., the light intensity falls in a range of 1500-3000 lx, 16 hours light/8 hours dark, culturing for 20-30 days.

(Seven) Seedling Hardening

The step of seedling hardening comprises: preparing the blueberry tissue culture seedlings that have been rooted, opening the cap of tissue culture bottle, adding 15 ml aseptic water therein, placing it in an environment where humidity is 70%, 1 day later, pouring off the water in the tissue culture bottle, and re-adding 20 mL sterile water, adjusting the humidity to 60% and performing the ventilation, transplanting 7 days later, the sterile water can be replaced once during the period. All the above light dark cycle is 16 hours light/8 hours darkness per day.

(Eight) Transplanting

Taking out the blueberry plants after seedling hardening from the bottle, removing the medium, using water to wash the root, sowing the plant into nutrition pot. The culture soil for transplanting is vermiculite: nutritious soil: moss (1:1:1 in mass ratio), pay attention to control the pH of nutrient soil to fall in a range of 5.3-5.6.

Example 3 takes explant as the material to conduct culture, observing the browning condition, and thus affect the final survival rate and production efficiency, increasing the workload and working time, thus the method is also suitable for the explant stem segment, the best material is also tissue culture seedling.

Comparative Example: Blueberry Tissue Culture

The difference from Example 2 is only lies in that the blueberry is not pre-cultured.

Figure 5:
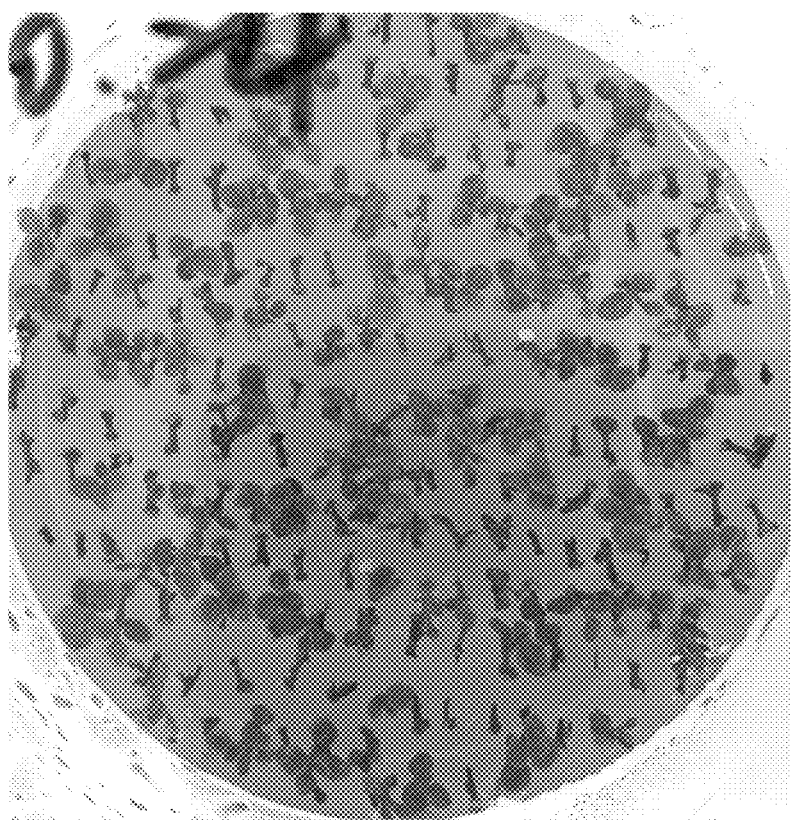
FIG. 5 shows the germination condition of blueberry stem segment upon rapid culture for 15 days.
Figure 6:
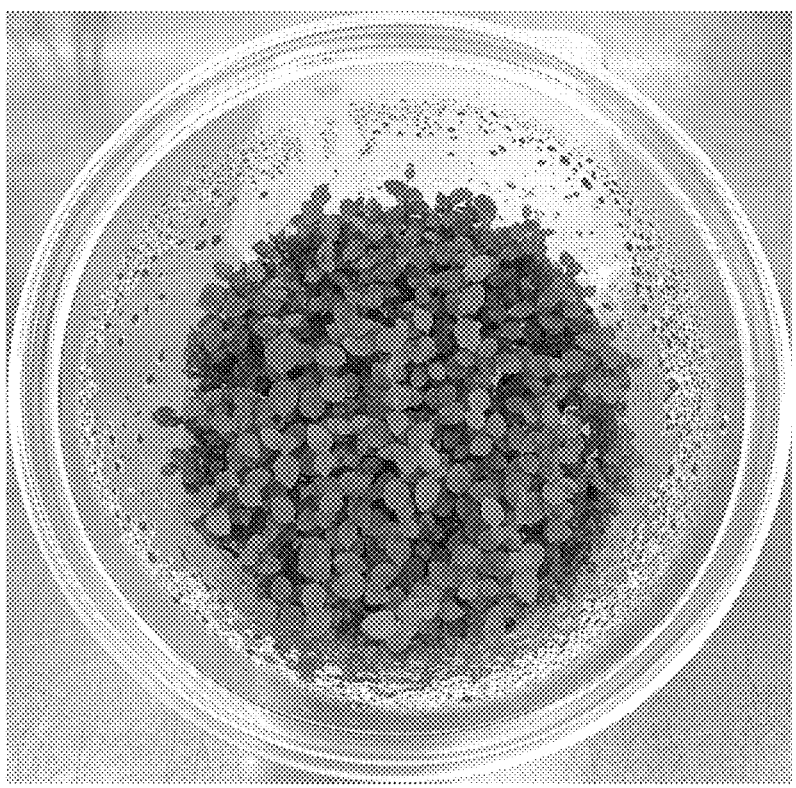
FIG. 6 shows the blueberry stem segment cultured on the rapid culture medium for 20 days.
Figure 10:
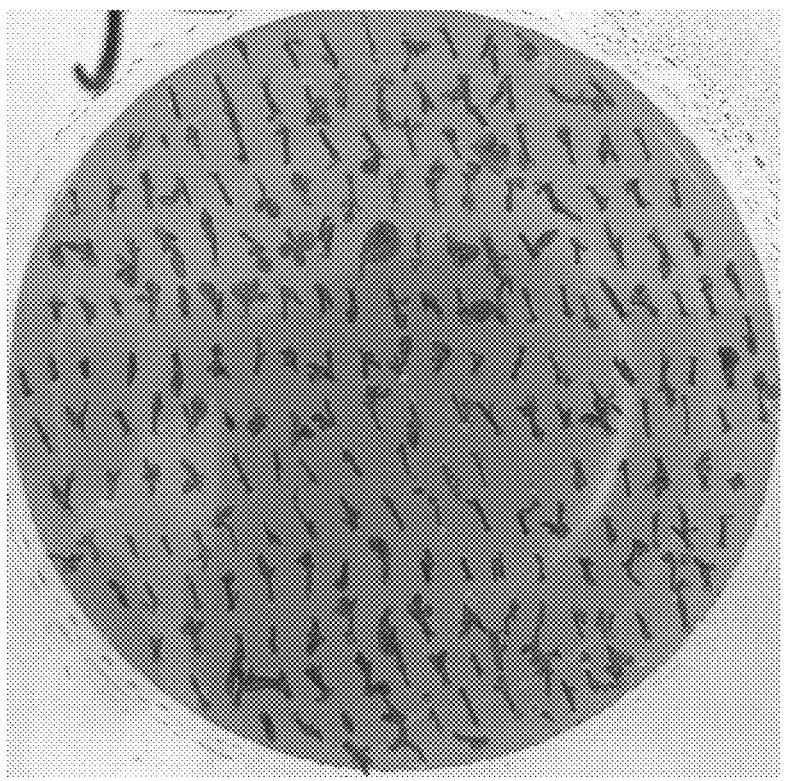
FIG. 10 shows the germination condition of the blueberry stem segment upon rapid culture for 15 days in comparative example.

In the rapid culture in this comparative Example, see FIG. 10 for photo of a bottle of rapid culture for 15 d, FIG. 5 and FIG. 10 are respectively the germination condition of the blueberry stem segment after 15 days of rapid culture of Example 2 and this comparative Example. In this Example, as no pre-culture was conducted to the blueberry, in the stage of rapid culture, the germination rate of the stem segment pre-cultured by rapid culture medium is slow, and the germination rate is low.

As can be known from technical common knowledge, the present invention can be achieved by other embodiments without separating the spiritual essence or essential features thereof. Therefore, in all aspects, all of the above disclosed embodiments are illustrated by examples, but not the only ones. All alterations in the scope of the present invention or equivalent to the scope of the present invention are included in the present invention.

What is claimed is:

1. A method of rapid propagation of blueberry stem segment tissue, comprising the following steps:
S1: inoculating the sterile blueberry stem segment with a bud point into the pre-culture medium to conduct pre-culture to obtain a pre-cultured blueberry stem segment, the pre-culture medium including
825 mg/L Ammonium Nitrate, 370 mg/L Magnesium Sulfate Heptahydrate, 950 mg/L Potassium Nitrate, 170 mg/L Potassium Dihydrogen, 220 mg/L Calcium chloride dihydrate, 6.2 mg/L Boric acid, 8.6 mg/L Zinc Sulfate Heptahydrate, 22.3 mg/L Manganese Sulfate Monohydrate, 0.25 mg/L Sodium Molybdate Dihydrate, 0.025 mg/L Cooper Sulfate Pentahydrate, 0.83 mg/L Potassium iodide, 0.025 mg/L Cobalt chloride hexahydrate, 40 mg/L ethylenediamine dihydroxyphenyl sodium iron acetate, 20 mg/L 2-(N-morpholine) ethanesulfonic acid, 100 mg/L Inositol, 2 mg/L Glycine, 0.1 mg/L Thiamine Hydrochloride, 0.5 mg/L Niacin, 0.5 mg/L Pyridoxine Hydrochloride, 0.1-0.5 mg/L IAA, 0.05-0.6 mg/L CPPU, 50-100 mg/L NaCl, 4-8 g/L agar and 15-30 g/L sucrose, with a pH in the range of 5.0-5.5;
S2: inoculating the pre-cultured blueberry stem segment into a rapid culture medium to conduct rapid culture to obtain rapid cultured blueberry seedlings, the rapid culture medium including
825 mg/L Ammonium Nitrate, 370 mg/L Magnesium Sulfate Heptahydrate, 950 mg/L Potassium Nitrate, 170 mg/L Potassium Dihydrogen, 220 mg/L Calcium chloride dihydrate, 6.2 mg/L Boric acid, 8.6 mg/L Zinc Sulfate Heptahydrate, 22.3 mg/L Manganese Sulfate Monohydrate, 0.25 mg/L Sodium Molybdate Dihydrate, 0.025 mg/L Cooper Sulfate Pentahydrate, 0.83 mg/L Potassium iodide, 0.025 mg/L Cobalt chloride hexahydrate, 40 mg/L ethylenediamine dihydroxyphenyl sodium iron acetate, 20 mg/L 2-(N-morpholine) ethanesulfonic acid, 100 mg/L Inositol, 2 mg/L Glycine, 0.1 mg/L Thiamine Hydrochloride, 0.5 mg/L Niacin, 0.5 mg/L Pyridoxine Hydrochloride, 0.2-0.5 mg/L ZT, 0.5-1.5 mg/L putrescine, 0.5-1.5 mg/L spermine, 0.5-1.5 mg/L spermidine, 4-8 g/L agar and 15-30 g/L sucrose, with a pH in the range of 5.0-5.5;
S3: inoculating the rapid cultured blueberry seedlings into a seedling growth medium to conduct continue culture to obtain further cultured blueberry seedlings, the seedling growth medium including
825 mg/L Ammonium Nitrate, 370 mg/L Magnesium Sulfate Heptahydrate, 950 mg/L Potassium Nitrate, 170 mg/L Potassium Dihydrogen, 220 mg/L Calcium chloride dihydrate, 6.2 mg/L Boric acid, 8.6 mg/L Zinc Sulfate Heptahydrate, 22.3 mg/L Manganese Sulfate Monohydrate, 0.25 mg/L Sodium Molybdate Dihydrate, 0.025 mg/L Cooper Sulfate Pentahydrate, 0.83 mg/L Potassium iodide, 0.025 mg/L Cobalt chloride hexahydrate, 40 mg/L ethylenediamine dihydroxyphenyl sodium iron acetate, 20 mg/L 2-(N-morpholine) ethanesulfonic acid, 100 mg/L Inositol, 2 mg/L Glycine, 0.1 mg/L Thiamine Hydrochloride, 0.5 mg/L Niacin, 0.5 mg/L Pyridoxine Hydrochloride, 0.5-1.5 mg/L 2-ip, 4-8mg/L agar and 15-30 g/L sucrose, with a pH in the range of 5.0-5.5; and
S4: inoculating the further cultured blueberry seedlings into a rooting medium to conduct continue culture to obtain blueberry tissue culture seedlings, the rooting medium including
950mg/L Potassium Nitrate, 166.1 mg/L Calcium Chloride, 825 mg/L Ammonium Nitrate, 90.35 mg/L Magnesium Sulfate, 85 mg/L Potassium Dihydrogen Phosphate, 0.025 mg/L Cooper Sulphate, 6.2 mg/L Boric Acid, 16.9 mg/L Manganese Sulfate, 0.25 mg/L Sodium Molybdate, 8.6 mg/L Zinc Sulfate, 0.025 mg/L Cobalt Chloride, 0.83 mg/L Potassium Iodide, 27.8 mg/L FeSO$_4$·7H$_2$O, 37.26 mg/L Na$_2$-EDTA·2H$_2$O, 2.0 mg/L Glycine, 100 mg/L Inositol, 0.50 mg/L Niacin, 0.1 mg/L Thiamine Hydrochloride, 0.5 mg/L Pyridoxine Hydrochloride, 1.0-3.0 mg/L NAA, 4-8 g/L agar and 15-30 g/L sucrose, with a pH in the range of 5.0-5.5.

2. The medium combination of claim 1, wherein, in the pre-culture medium, the concentration of IAA falls in a range of 0.15-0.3 mg/L and the concentration of CPPU falls in a range of 0.05-0.3 mg/L; or
in the rapid culture medium, the concentration of ZT falls in a range of 0.3-0.5 mg/L; or
in the seedling growth medium, the concentration of 2-ip is 0.5 mg/L; or
in the rooting medium, the concentration of NAA is 2.0 mg/L.

3. The medium combination of claim 2, wherein, in the pre-culture medium, the concentration of IAA is 0.2 mg/L and the concentration of CPPU is 0.1 mg/L; or
in the rapid culture medium, the concentration of ZT is 0.4 mg/L.

4. The method of claim 1, wherein, in step S1, the sterile blueberry stem segment is from the blueberry tissue culture seedlings;
the pre-culture is conducted in dark environment at 10-20° C. for 1-4 hours, and then under light-dark conditions for 1-3 days at a humidity in the range of 50-70%, the light-dark conditions comprising 14-18hours of light per day at a light intensity in a range of 1500-3000lx with darkness for the remained of each day.

5. The method of claim 1, wherein, in step S2, a culture temperature falls in a range of 20–28° C.;
a culture light time falls in a range of 14-18 hours a day, with darkness for the remainder of each day;
a culture light intensity falls in a range of 1500-3000 lx;
a culture environment humidity falls in a range of 50-70%; and
a culture time falls in a range of 15-20 days.

6. The method of claim 1, wherein, in step S3, a culture temperature falls in a range of 20–28° C.;
a culture light time falls in a range of 14-18 hours a day, with darkness for the remainder of each day;
a culture light intensity falls in a range of 1500-3000 lx;
a culture environment humidity falls in a range of 50-70%;
a the culture time falls in a range of 10-20 days.

7. The method of claim 1, wherein, in step S4, culture temperature falls in a range of 20–28° C.;
culture light time falls in a range of 14-18 hours a day, with darkness for the remainder of each day;
a culture light intensity falls in a range of 1500-3000 lx;

a culture environment humidity falls in a range of 50-70%; and a culture time falls in a range of 20-30 days.

8. The method of claim 1, wherein the method further comprises: conducting seedling hardening and transplanting to the blueberry tissue culture seedlings to obtain blueberry cultivated plant.

9. The method of claim 1, wherein neither callus induction nor budding via callus occurs.

* * * * *